(12) United States Patent
Rodeheaver et al.

(10) Patent No.: US 12,350,145 B2
(45) Date of Patent: Jul. 8, 2025

(54) MAGNETICALLY COUPLED POWER DELIVERY FOR SURGICAL IMPLANTS

(71) Applicant: Alcon Inc., Fribourg (CH)

(72) Inventors: Austin Xavier Rodeheaver, Arlington, TX (US); Todd Taber, Keller, TX (US); John Briant, Royston (GB); Grant Corthorn, Royston (GB); Rob May, Royston (GB); Martin Orrell, Royston (GB); Trevor Penhallurick, Royston (GB); David Pooley, Royston (GB); Catherine Wyman, Royston (GB); Charlie Constable, Royston (GB)

(*) Notice: Subject to any disclaimer, the term of this patent is extended or adjusted under 35 U.S.C. 154(b) by 645 days.

(21) Appl. No.: 17/647,909

(22) Filed: Jan. 13, 2022

(65) Prior Publication Data

US 2022/0226104 A1 Jul. 21, 2022

Related U.S. Application Data

(60) Provisional application No. 63/137,841, filed on Jan. 15, 2021.

(51) Int. Cl.
*A61F 2/16* (2006.01)
*A61B 90/00* (2016.01)
*A61F 9/00* (2006.01)

(52) U.S. Cl.
CPC .......... *A61F 2/1662* (2013.01); *A61B 90/08* (2016.02); *A61F 2/167* (2013.01); *A61F 9/0017* (2013.01); *A61B 2090/0813* (2016.02)

(58) Field of Classification Search
CPC .... A61F 2/1662; A61F 2/1664; A61F 2/1667; A61F 2/167; A61F 2/1672; A61F 2/1675; A61F 2/1678; A61F 9/0008; A61F 9/0017; A61F 9/00736; A61B 90/08; A61B 2090/0813; A61B 17/3468; A61B 17/50
See application file for complete search history.

(56) References Cited

U.S. PATENT DOCUMENTS

| | | |
|---|---|---|
| 7,156,854 B2 | 1/2007 | Brown et al. |
| 8,308,736 B2 | 11/2012 | Boukhny et al. |
| 8,308,799 B2 | 11/2012 | Chen et al. |
| 8,377,076 B2 | 2/2013 | Downer et al. |
| 8,801,780 B2 | 8/2014 | Chen |
| 9,480,555 B2 | 11/2016 | Downer et al. |
| 10,172,706 B2 | 1/2019 | Auld et al. |
| 10,568,735 B2 | 2/2020 | Brown et al. |
| 10,588,780 B2 | 3/2020 | Van Noy et al. |
| 11,039,953 B2 | 6/2021 | Balachandran |
| 12,004,944 B2 | 6/2024 | Weston |
| 2008/0097460 A1 | 4/2008 | Boukhny et al. |
| 2008/0221584 A1 | 9/2008 | Downer |
| 2010/0057093 A1 | 3/2010 | Ide et al. |

(Continued)

FOREIGN PATENT DOCUMENTS

| | | |
|---|---|---|
| DE | 102019115125 B3 | 9/2020 |
| JP | 2007190360 A | 8/2007 |

(Continued)

*Primary Examiner* — Kathleen S Holwerda

(57) ABSTRACT

A magnetically coupled drive module for delivering an implant to an eye. An implant may be stored, advanced, and delivered to an eye using a powered drive module. The drive module may be decoupled and sterilized for reuse.

14 Claims, 9 Drawing Sheets

(56) References Cited

U.S. PATENT DOCUMENTS

| | | | |
|---|---|---|---|
| 2011/0265779 A1 | 11/2011 | Vandrak et al. | |
| 2012/0022548 A1* | 1/2012 | Zacharias | A61F 2/1672 606/107 |
| 2013/0197532 A1 | 8/2013 | Boukhny et al. | |
| 2013/0253527 A1 | 9/2013 | Schneider et al. | |
| 2015/0238687 A1 | 8/2015 | Novakovic et al. | |
| 2015/0282928 A1 | 10/2015 | Auld et al. | |
| 2016/0087460 A1 | 3/2016 | Rich et al. | |
| 2017/0007237 A1 | 1/2017 | Yates et al. | |
| 2017/0027686 A1 | 2/2017 | Nagasaka | |
| 2017/0119522 A1 | 5/2017 | Auld et al. | |
| 2018/0049866 A1 | 2/2018 | Fayyaz et al. | |
| 2018/0200046 A1 | 7/2018 | Brown et al. | |
| 2020/0179101 A1 | 6/2020 | Flowers et al. | |
| 2020/0179102 A1 | 6/2020 | Chen et al. | |
| 2020/0179103 A1 | 6/2020 | Auld et al. | |
| 2020/0188089 A1 | 6/2020 | Auld et al. | |
| 2020/0197170 A1 | 6/2020 | Auld et al. | |
| 2021/0052371 A1 | 2/2021 | Singh et al. | |
| 2022/0265420 A1* | 8/2022 | Kelp | A61F 2/167 |

FOREIGN PATENT DOCUMENTS

| | | | |
|---|---|---|---|
| WO | 9637152 A1 | 11/1996 | |
| WO | 2020065516 A1 | 4/2020 | |
| WO | 2020128762 A1 | 6/2020 | |

\* cited by examiner

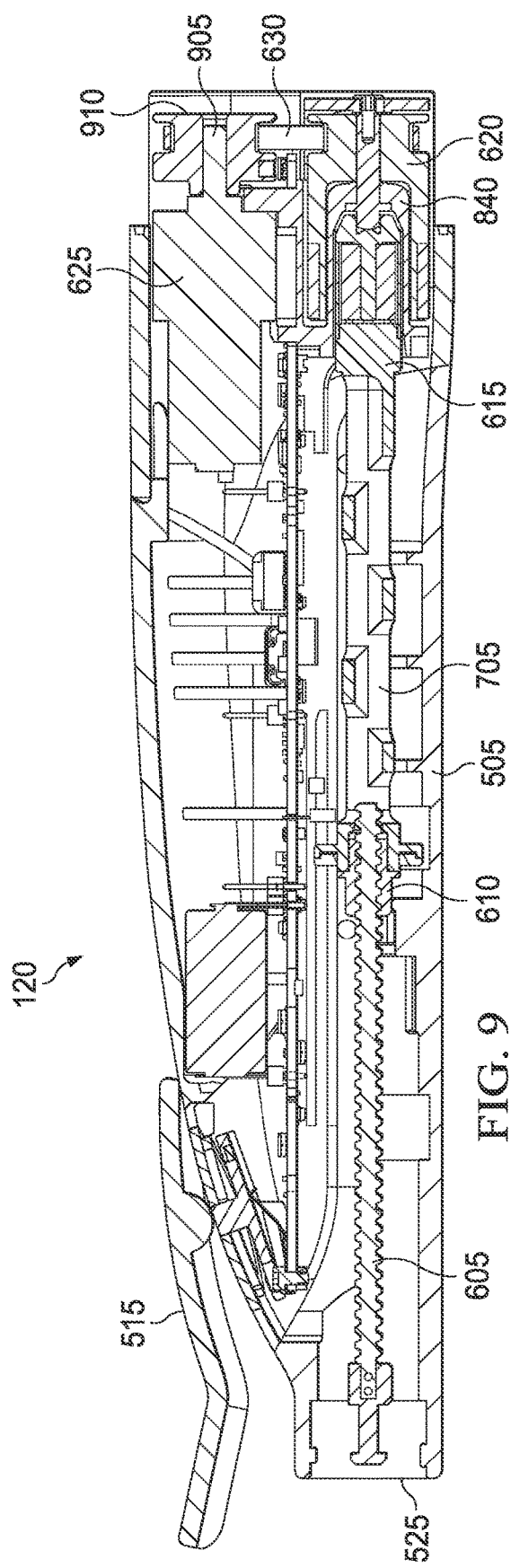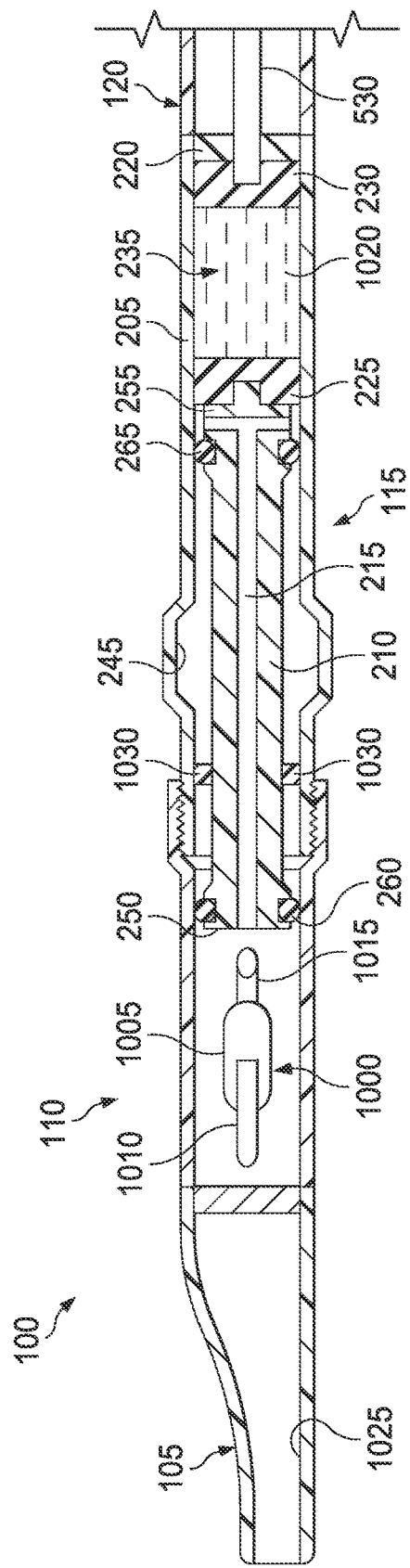

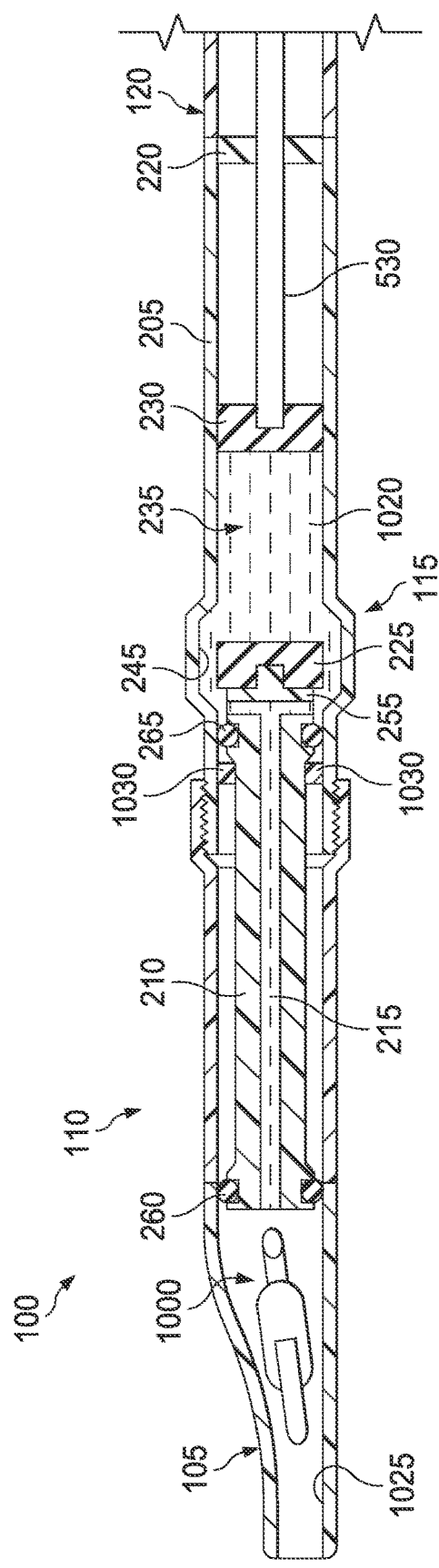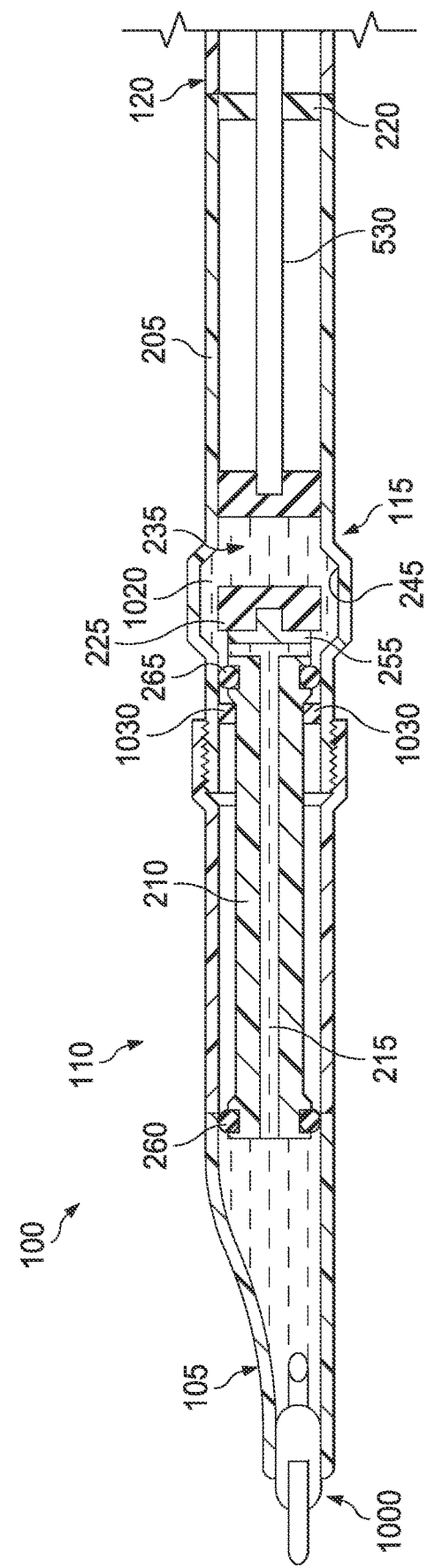
FIG. 10B
FIG. 10C

MAGNETICALLY COUPLED POWER DELIVERY FOR SURGICAL IMPLANTS

PRIORITY CLAIM

This application claims the benefit of priority of U.S. Provisional Patent Application Ser. No. 63/137,841 titled "MAGNETICALLY COUPLED POWER DELIVERY FOR SURGICAL IMPLANTS," filed on Jan. 15, 2021, whose inventors are Austin Xavier Rodeheaver, Todd Taber, John Briant, Grant Corthorn, Rob May, Martin Orrell, Trevor Penhallurick, David Pooley and Catherine Wyman, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may comprise or consist essentially of an apparatus for delivering an implant, such as an intraocular lens, using hydraulic pressure or fluid flow. In more particular examples, the apparatus may comprise a rigid plunger for advancing an implant. Some embodiments may additionally comprise a bore through the rigid plunger, which can allow a working fluid to advance the implant into the eye via hydraulic pressure in a second phase. For example, a hollow rigid plunger can be used to first advance an intraocular lens to a point that a seal is created about the intraocular lens within a delivery lumen. The lens may then be hydraulically advanced to delivery by passing a working fluid through the hollow bore of the plunger.

In some embodiments, a powered drive module may be advantageous for advancing the plunger. For example, a drive module may comprise a drive shaft, which can be operated by a battery-powered motor to advance the plunger. Some embodiments of the drive shaft may be magnetically coupled to the motor, allowing the motor, battery, and other reusable electronic components to be completely sealed. In more particular examples, concentric or complementary rings of magnets may be used to couple the motor to the drive shaft. The motor can rotate the outer magnetic ring, which can rotate the inner magnetic ring. In some embodiments, the drive shaft may comprise a lead screw, which can be advanced or retracted by rotation of the inner magnetic ring.

More generally, an apparatus for operating an implant delivery device may comprise a lead screw, a lead nut threaded to the lead screw, a follower coupled to the lead nut, a driver magnetically coupled to the follower, a containment seal between the driver and the follower, and a motor coupled to the driver. A containment seal can fluidly isolate the driver from the follower. In more particular embodiments, the apparatus may comprise a lead sleeve that couples the follower to the lead nut. For example, the lead sleeve may comprise an open cylinder configured to receive at least a portion of the lead screw. In some embodiments, the follower may comprise a first magnetic rotor, and the driver may comprise a second magnetic rotor. The second magnetic rotor may have an open cylinder disposed concentrically around the first magnetic rotor in some embodiments. Some embodiments of the follower or the first magnetic rotor may comprise a first plurality of magnets, and the driver or second magnetic rotor may comprise a second plurality of magnets. The first plurality of magnets may be disposed in a cylindrical array, and the second plurality of magnets may be disposed in a cylindrical array around the first plurality of magnets. The first plurality of magnets and the second plurality of magnets may be arranged with alternating polarity in some embodiments.

In other embodiments, an apparatus for delivering an implant to an eye may comprise a nozzle, an actuator, a motor magnetically coupled to the actuator, and a containment seal that fluidly isolates the motor from the actuator. The motor may be configured to operate the actuator to eject the implant through the nozzle.

In more particular embodiments, an apparatus for delivering an implant to an eye may comprise a nozzle having a delivery lumen, an implant bay coupled to the nozzle, and an actuator. A follower may be coupled to the actuator, and a driver may be magnetically coupled to the follower. A containment seal may be disposed between the driver and the follower. The driver may be coupled to a motor, which can be configured to operate the driver to move the follower to cause the actuator to engage the implant in the implant bay and move the implant through the delivery lumen. The actuator may comprise a housing and a plunger operable to move linearly within the housing, and the follower may be coupled to the plunger.

A method for using an implant delivery apparatus may comprise providing an implant in an implant bay of the implant delivery apparatus, magnetically coupling a drive shaft to a drive module of the implant delivery apparatus, coupling the drive shaft to an actuator of the implant delivery apparatus, operating the drive module to advance the implant from the implant bay through a delivery lumen with the drive shaft and the actuator, removing the drive shaft from the drive module, and sterilizing the drive module.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

FIG. 9 is a section view of the drive module of FIG. 5.

FIGS. 10A-10C are schematic diagrams illustrating an example method of ejecting an implant from the system of FIG. 2.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
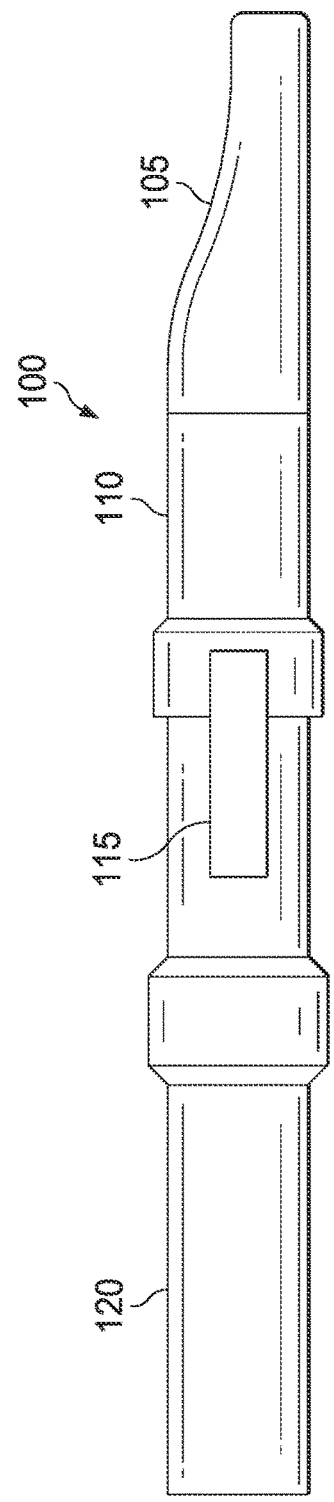
FIG. 1 is a schematic view of an example system for inserting an implant into an eye.

FIG. 1 is a schematic diagram of a system 100 that can insert an implant into an eye. In some embodiments, the system 100 may comprise two or more modules, which can be configured to be coupled and decoupled as appropriate for storage, assembly, use, and disposal. For example, as illustrated in FIG. 1, some embodiments of the system 100 may include a nozzle 105, an implant bay 110 coupled to the nozzle 105, and an actuator 115 coupled to the implant bay 110. In some embodiments, the system 100 may additionally comprise a drive module 120 configured to engage the actuator 115.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to extend or splay one or more features, such as haptics, of an intraocular lens.

The actuator 115 is generally configured to advance an implant from the implant bay 110 into the nozzle 105, and thereafter from the nozzle 105 through an incision and into an eye.

The drive module 120 is generally operable to energize the actuator 115. In some examples, the drive module 120 may be operated by electrical, mechanical, hydraulic, or pneumatic power, or combinations thereof, or in some other manner. In some instances, the drive module 120 may be operated manually. According to other implementations, the drive module 120 may be an automated system.

In general, components of the system 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically coupled to the drive module 120 and may be mechanically and fluidly coupled to the nozzle 105. In some embodiments, components may also be coupled by virtue of physical proximity, being integral to a single structure, or being formed from the same piece of material.

Figure 2:
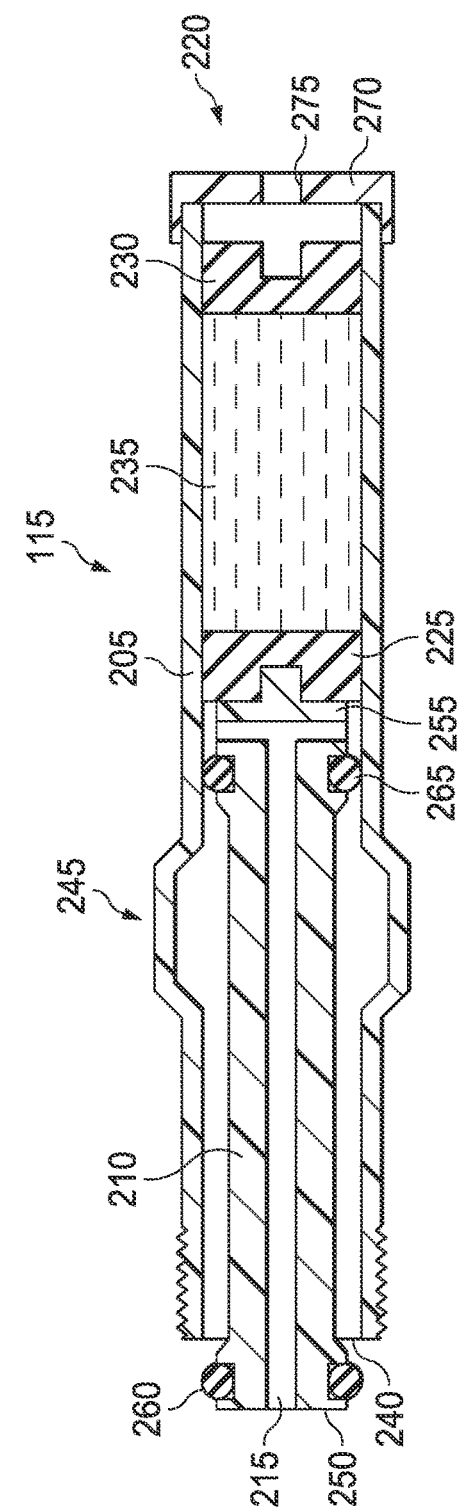
FIG. 2 is a schematic diagram of an actuator that may be associated with some examples of the system of FIG. 1.

FIG. 2 is a schematic diagram of an example of the actuator 115, illustrating additional details that may be associated with some embodiments. The actuator 115 of FIG. 2 generally comprises a housing 205 and a plunger 210 disposed within the housing 205. The plunger 210 is generally comprised of a substantially rigid material, such as a medical grade polymer material. In the example of FIG. 2, the actuator 115 further comprises a bore 215 through the plunger 210, and a drive interface 220 configured to couple with the drive module 120 (FIG. 1). A plunger seal 225 may be disposed within the housing 205 and coupled to the plunger 210. A drive seal 230 may also be disposed within the housing 205.

As illustrated in the example of FIG. 2, the drive seal 230 may be disposed between the plunger seal 225 and the drive interface 220, and a fluid chamber 235 may be defined within the housing 205 between the plunger seal 225 and the drive seal 230. In the example configuration of FIG. 2, the plunger seal 225 is configured to provide a fluid seal across the housing 205 and substantially prevent movement of fluid from the fluid chamber 235 to the bore 215. The drive seal 230 may also be configured to provide a fluid seal across the housing 205 and substantially prevent movement of fluid from the fluid chamber 235 to the drive interface 220.

The housing 205 of FIG. 2 further comprises a plunger interface 240 and a bypass channel 245 disposed between the plunger interface 240 and the drive interface 220. The bypass channel 245 may take various forms. For example, the bypass channel 245 may comprise a protrusion in the housing 205, as illustrated in FIG. 2. In other examples, the bypass channel 245 may comprise a groove or recess in the inner surface of the housing 205. In some embodiments, the bypass channel 245 may comprise a plurality of channels.

For example, a plurality of channels may be disposed circumferentially around the housing 205 in some embodiments.

The plunger 210 generally has a first end 250 and a second end 255, wherein the first end 250 is generally disposed adjacent to the plunger interface 240. The bore 215 generally passes through the plunger 210 longitudinally from the first end 250 to the second end 255.

In some embodiments, the actuator 115 may additionally comprise a nozzle seal 260 and a bypass seal 265. Each of the nozzle seal 260 and the bypass seal 265 may be generally configured to create a seal between a portion of the plunger 210 and the housing 205 to substantially prevent movement of fluid past the seal. As illustrated in the example of FIG. 2, one or both of the nozzle seal 260 and the bypass seal 265 may be ring seals, such as an O-ring, disposed circumferentially around a portion of the plunger 210. In other examples, an umbrella seal may be suitable. In more particular embodiments, the nozzle seal 260 may be disposed proximate to the first end 250 of the plunger 210, and the bypass seal 265 may be disposed proximate to the second end 255 of the plunger 210.

The drive interface 220 of FIG. 2 comprises a cap 270 and an aperture 275. The cap 270 may be coupled to an end of the housing 205 to retain the drive seal 230 and other components within the housing 205.

Figure 3:
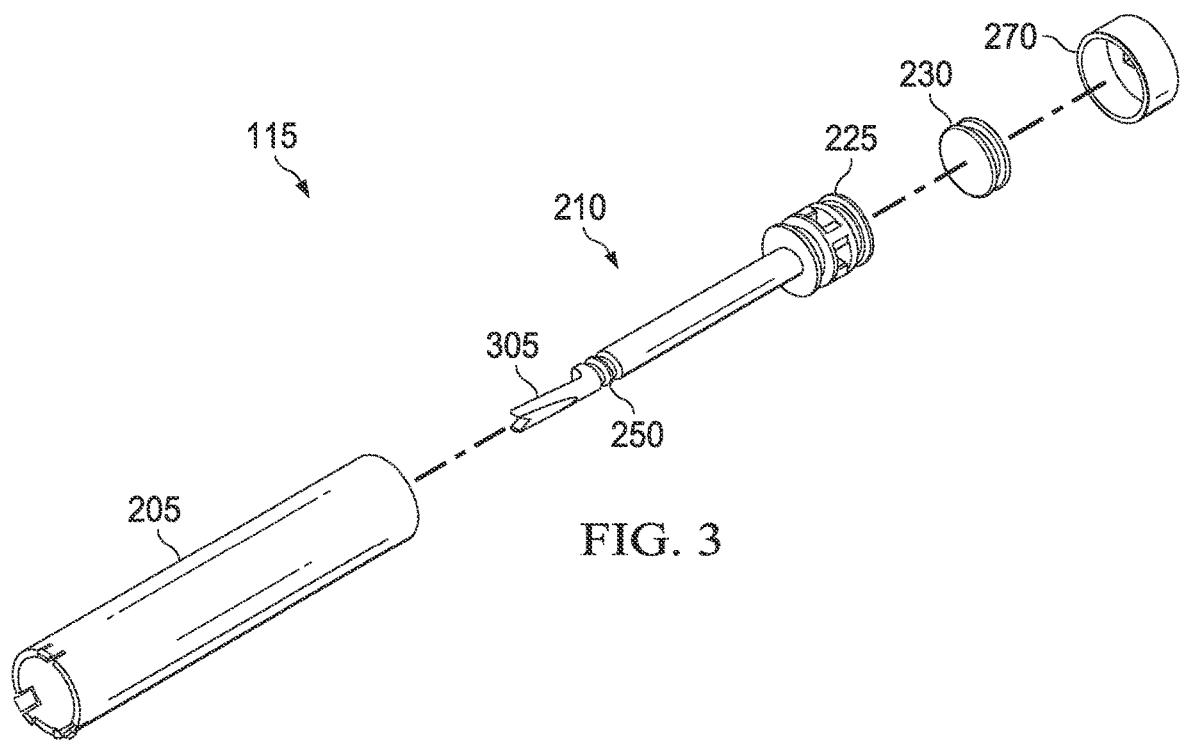
FIG. 3 is an assembly view of an example of the actuator of FIG. 2.

FIG. 3 is an assembly view of another example of the actuator 115 of FIG. 1, illustrating additional details that may be associated with some embodiments. For example, the housing 205 of FIG. 3 comprises a hollow cylinder, which can receive the plunger 210, the plunger seal 225, and the drive seal 230. FIG. 3 also illustrates an example of an implant interface 305, which may be coupled to the first end 250 of the plunger 210 in some embodiments. In the example of FIG. 3, the plunger 210 and the plunger seal 225 may be inserted into the housing 205, and then a suitable working fluid may be added before inserting the drive seal 230 and attaching the cap 270 to the housing 205.

Figure 4:
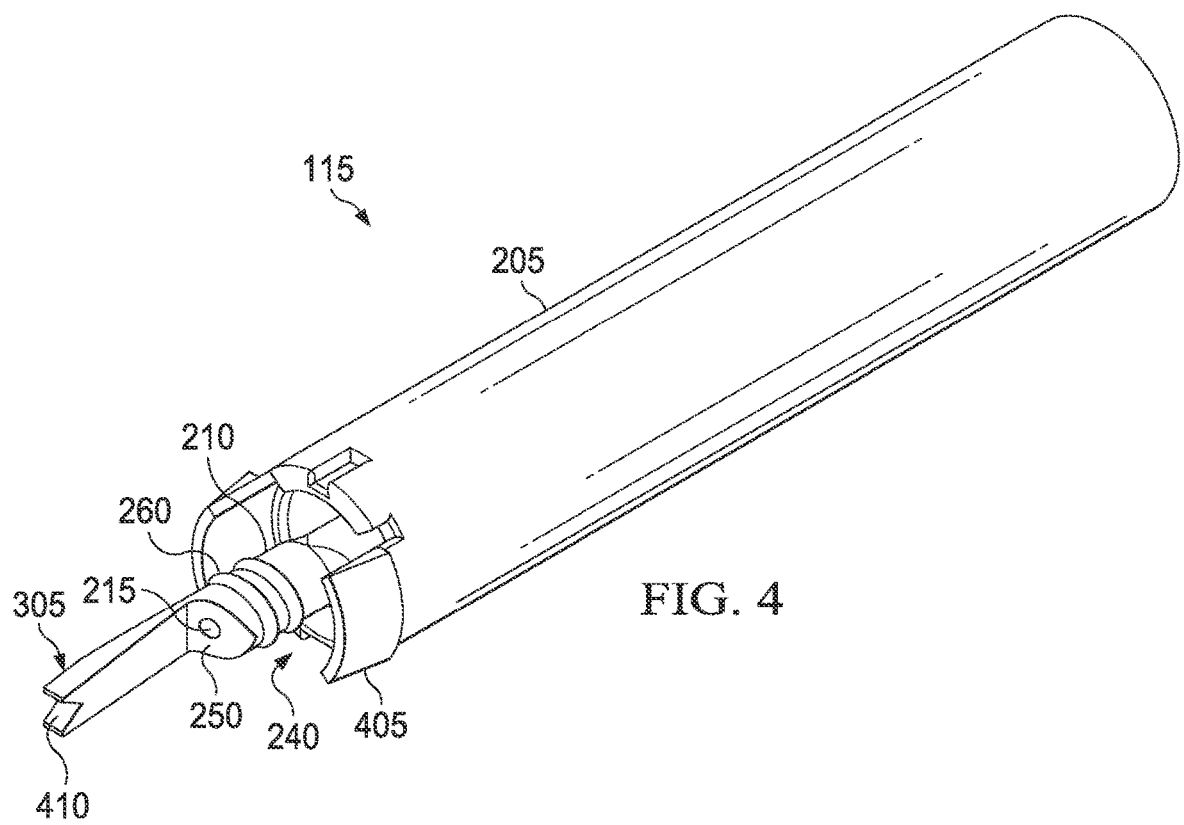
FIG. 4 is an isometric view of the actuator of FIG. 3, as assembled.

FIG. 4 is an isometric view of the actuator 115 of FIG. 3, as assembled. As illustrated in the example of FIG. 4, some embodiments of the plunger interface 240 may comprise an opening in the housing 205 and one or more locking tabs 405. The implant interface 305 and at least a portion of the plunger 210 may extend through the plunger interface 240. The nozzle seal 260 of FIG. 4 comprises at least one O-ring disposed around the plunger 210 adjacent to the first end 250. As seen in the example of FIG. 4, the bore 215 may define an opening in the first end 250. In some embodiments, the opening may be centrally disposed through the first end 250, and the implant interface 305 may be coupled to the plunger 210 adjacent to the opening in the first end 250. The implant interface 305 may comprise a notch 410, which may be configured to engage an implant.

Figure 5:
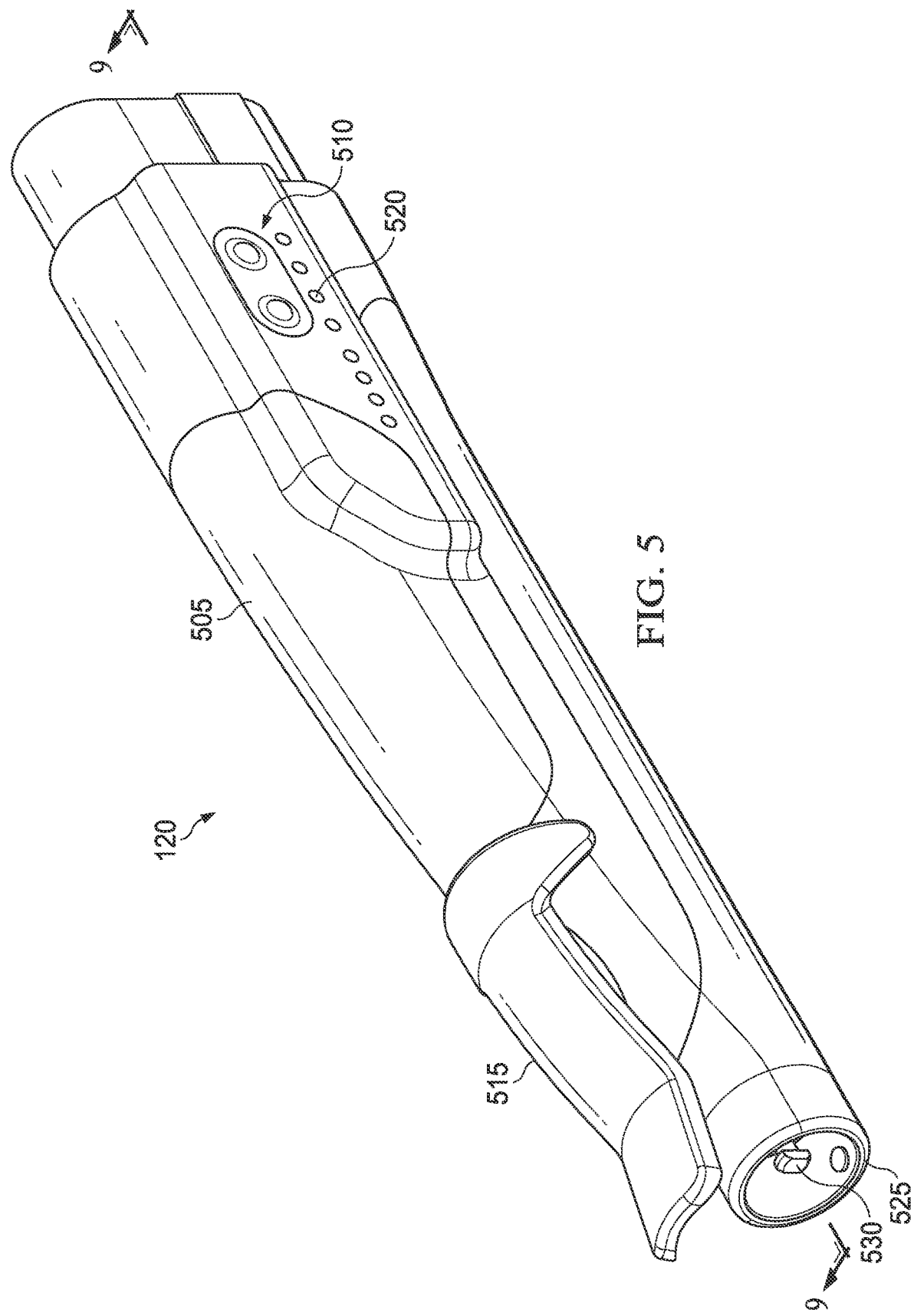
FIG. 5 is an isometric view of an example of a drive module that may be associated with some embodiments of the system of FIG. 1.

FIG. 5 is an isometric view of an example of the drive module 120 of FIG. 1, illustrating additional details that may be associated with some embodiments. For example, the drive module 120 of FIG. 5 comprises a housing 505, a user interface 510, and a control switch 515. In some embodiments, the user interface 510 may comprise one or more visual output devices, such as light-emitting diodes 520, which can indicate various operating states. In other examples, the user interface 510 may comprise a display screen, such as a liquid-crystal display. Additionally, or alternatively, the user interface 510 may comprise one or more audio output devices, tactile output devices, or both. The housing 505 may define an actuator interface 525, which may be configured to be coupled to the actuator 115, for example. An example of a drive shaft 530 is also illustrated in the example of FIG. 5. In general, the drive shaft 530 may move through the actuator interface 525.

Figure 6:
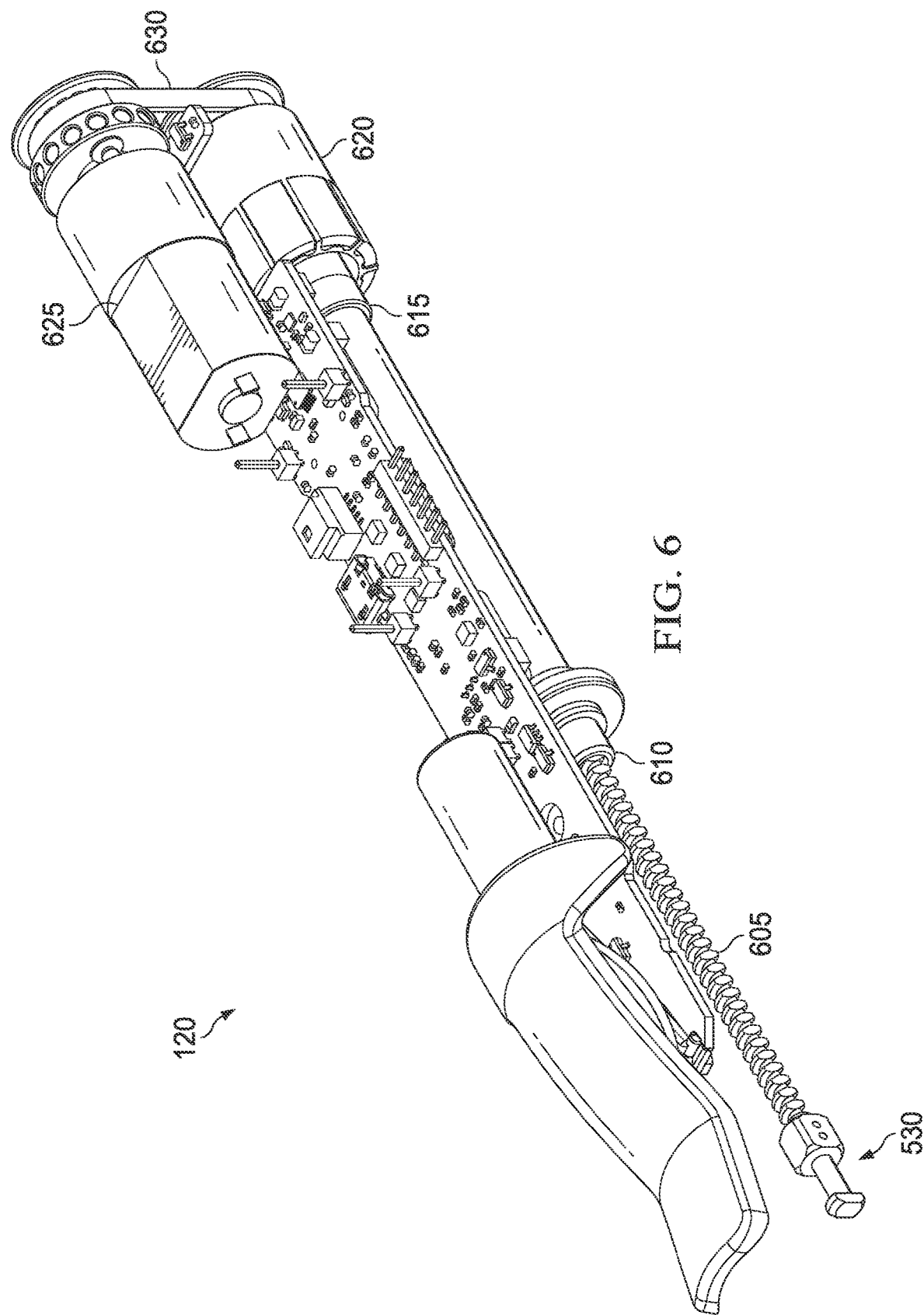
FIG. 6 is an internal view of the drive module of FIG. 5.

FIG. 6 is an isometric view of the drive module 120 of FIG. 5 with the housing 505 removed to illustrate additional details that may be associated with some embodiments. As illustrated in FIG. 6, some embodiments of the drive shaft 530 may comprise a lead screw 605 and a lead nut 610, which may be threaded onto the lead screw 605. The drive shaft 530 may additionally comprise a follower 615, which may be magnetically coupled to a driver 620. The driver 620 may be coupled to a motor 625. For example, in some embodiments, a drive belt 630 may couple the motor 625 to the driver 620 as illustrated in the example of FIG. 6.

Figure 7:
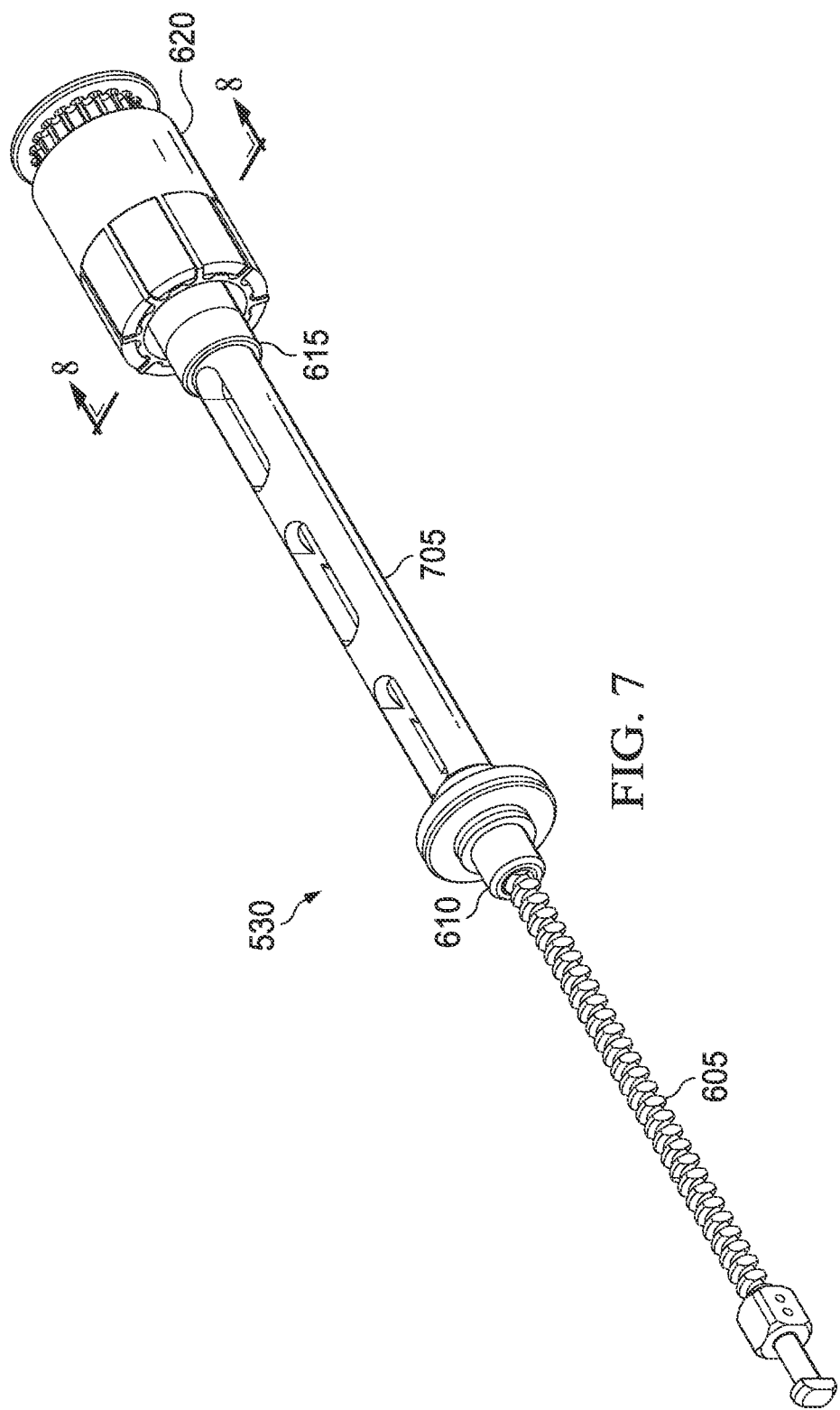
FIG. 7 is an isometric view of a drive assembly that may be associated with the drive module of FIG. 6.

FIG. 7 is an isometric view of the drive shaft 530 and the driver 620 of FIG. 6, illustrating additional details that may be associated with some embodiments. For example, the follower 615 may be coupled to the lead nut 610. In more particular embodiments, the drive shaft 530 may comprise a lead sleeve 705, which can couple the follower 615 to the lead nut 610 as illustrated in the example of FIG. 7. The lead sleeve 705 of FIG. 7 generally comprises an open cylinder configured to receive at least a portion of the lead screw 605.

Figure 8:
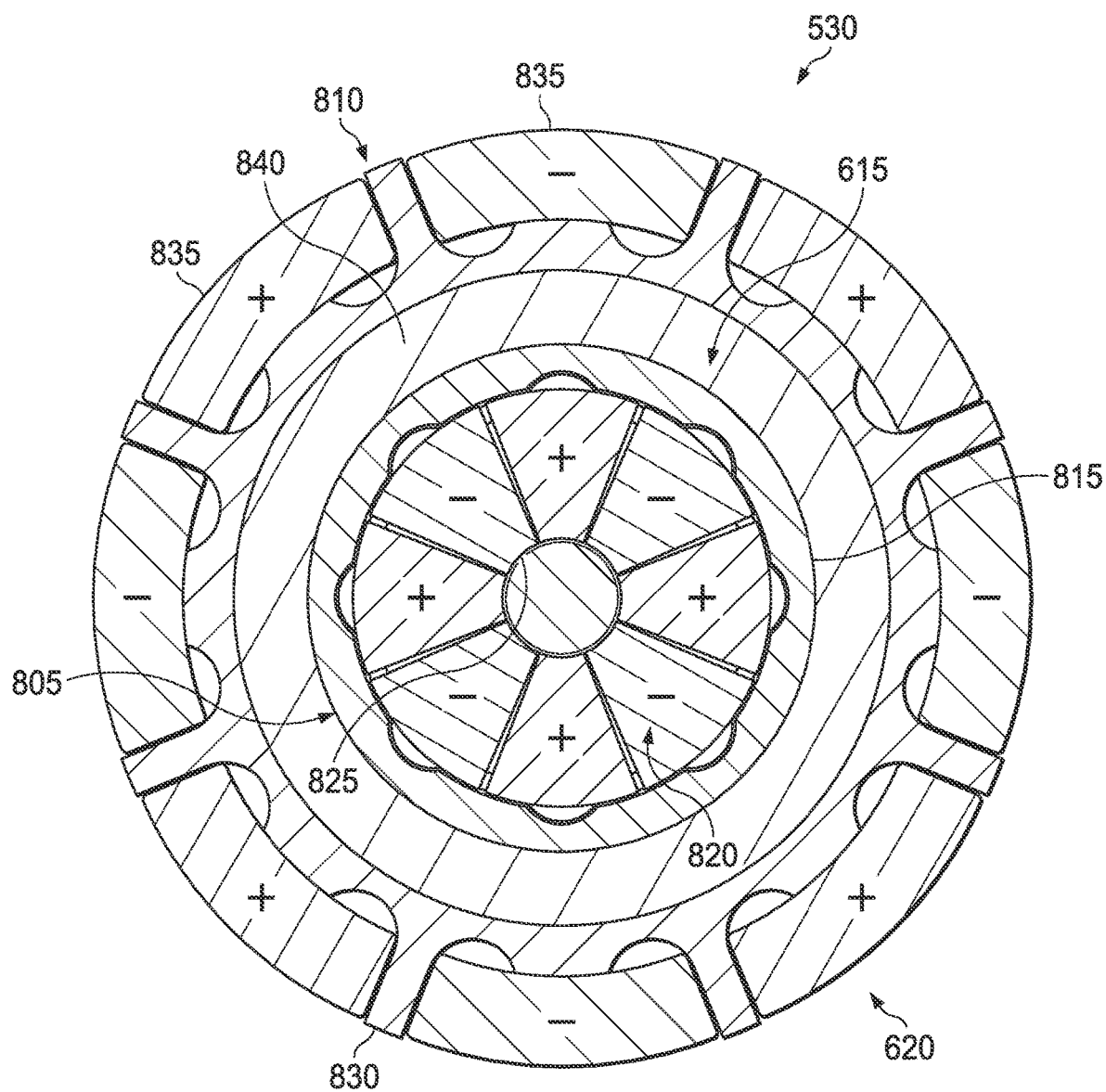
FIG. 8 is a section view of the drive assembly of FIG. 7.

FIG. 8 is a section view of the drive shaft 530 of FIG. 7, taken along line 8-8, illustrating additional details that may be associated with some embodiments. In the example of FIG. 8, the follower 615 comprises a first magnetic rotor 805, and the driver 620 comprises a second magnetic rotor 810. The second magnetic rotor 810 of FIG. 8 comprises an open cylinder disposed concentrically around the first magnetic rotor 805. In some embodiments, the first magnetic rotor 805 may comprise first housing 815 and a first plurality of magnets 820 disposed within the first housing 815. As illustrated in FIG. 8, the first housing 815 may have a housing core 825 in some embodiments. In other examples, the first housing 815 may be hollow. In the example of FIG. 8, the first plurality of magnets 820 are arranged concentrically around the housing core 825. The first plurality of magnets 820 may be bonded to the surface of the first housing 815 in some embodiments. The second magnetic rotor 810 may comprise a second housing 830 and a second plurality of magnets 835. The second plurality of magnets 835 may be supported by the second housing 830 in a cylindrical array concentrically around the first plurality of magnets 820. A containment seal 840 may be disposed between the follower 615 and the driver 620. In some embodiments, the first plurality of magnets 820 and the second plurality of magnets 835 are arranged with alternating polarity, as illustrated in the example of FIG. 8.

FIG. 9 is a section view of the drive module 120 of FIG. 5, taken along line 9-9 to illustrate additional details that may be associated with some embodiments. As illustrated in the example of FIG. 9, the lead nut 610 may be threaded to the lead screw 605, and the lead sleeve 705 may rigidly couple the follower 615 to the lead nut 610. For example, the lead sleeve 705 may be bonded to the lead nut 610 in some embodiments. In other examples, the lead nut 610 and the lead sleeve 705 may be integrally molded. The follower 615 may also be bonded to the lead sleeve 705. As illustrated in the example of FIG. 9, the containment seal 840 may fluidly isolate the follower 615 from the driver 620. For example, the containment seal 840 may comprise or consist essentially of a sleeve or shroud of a liquid-impermeable material disposed between the driver 620 and the follower 615. In some embodiments, the containment seal 840 may be coupled to the housing 505 to fluidly isolate the driver 620, the motor 625, and other components within the housing.

The driver 620 may be magnetically coupled to the follower 615 through the containment seal 840, allowing the follower 615 to freely rotate within the containment seal 840 and the driver 620 to freely rotate around the containment seal 840.

In operation, the follower 615 may be inserted into the containment seal 840 to magnetically couple the follower 615 to the driver 620. The control switch 515 may be pressed or otherwise activated to operate the motor 625, which can rotate a motor pin 905. In some embodiments, the motor pin 905 may be rigidly coupled to an output wheel 910, which can rotate with the motor pin 905. Rotation of the output wheel 910 can rotate the drive belt 630, which can rotate the driver 620. The magnetic force between the driver 620 and the follower 615 can cause the follower 615 to rotate with the driver 620, which can rotate the lead sleeve 705 and the lead nut 610. In some embodiments, the lead screw 605 may have a flat side (see FIG. 7), and some portion of the housing 505 may be configured to engage the flat side of the lead screw 605 to prevent rotation. Preventing rotation of the lead screw 605 allows rotation of the lead nut 610 to advance or retract the lead screw 605 linearly. In the example of FIG. 9, the lead screw 605 may be advanced or retracted through the actuator interface 525.

FIGS. 10A-10C are schematic diagrams illustrating an example method of ejecting an implant 1000 from the system 100. Initially, various components of the system 100 may be assembled if needed. For example, the nozzle 105, the implant bay 110, and the actuator 115 may be coupled to each other as illustrated in FIG. 10A. The drive module 120 may also be coupled to the actuator 115 through the drive interface 220. For example, the actuator interface 525 may be configured to align with and be coupled to the drive interface 220 in some embodiments. In some embodiments, the drive shaft 530 may be configured to directly engage the drive seal 230 through the drive interface 220, as illustrated in FIG. 10A. In other examples, the drive shaft 530 may be configured to engage the drive seal 230 through the drive interface 220.

The implant 1000 may be provided in the implant bay 110, as illustrated in the example of FIG. 10A. In some embodiments, the implant 1000 may comprise an intraocular lens, which may have a shape similar to that of a natural lens of an eye, and it may be made from numerous materials. In the example of FIG. 10A, the implant 1000 is illustrative of an intraocular lens having an optic body 1005, a leading haptic 1010, and a trailing haptic 1015. Examples of suitable materials may include silicone, acrylic, and combinations of such suitable materials. In some instances, the implant 1000 may comprise an intraocular lens that is fluid-filled, such as a fluid-filled accommodating intraocular lens.

In some examples, a working fluid 1020 may be stored in the fluid chamber 235. In FIG. 7, for example, the plunger seal 225 fluidly isolates the bore 215 from the working fluid 1020 in the fluid chamber 235, which can allow the working fluid 1020 to be stored within the fluid chamber 235 before use. In some examples, the nozzle seal 260 and the first end 250 of the plunger 210 may protrude into the implant bay 110, as illustrated in FIG. 10A, which can create a seal in the implant bay 110 behind the implant 1000. The first end 250 of the plunger 210 may also engage the implant 1000, in some examples. In other examples, the nozzle seal 260 and the first end 250 may be contained within the housing 205 before use.

The plunger 210, the plunger seal 225, and the drive seal 230 are generally movable within the housing 205. For example, in some embodiments, the drive module 120 may move the drive shaft 530 against the drive seal 230, which can rigidly move the plunger 210, the plunger seal 225, the drive seal 230, and the working fluid 1020, maintaining a fixed relationship as illustrated in FIG. 10B. For example, the control switch 515 may be activated to operate the motor 625 to advance the drive shaft 530, which can move the plunger 210, the plunger seal 225, the drive seal 230, and the working fluid 1020 from the configuration of FIG. 10A to the configuration of FIG. 10B.

Movement of the plunger 210 can advance the implant 1000 into a delivery lumen 1025 of the nozzle 105, which may create a fluid seal between the implant 1000 and the delivery lumen 1025. In some examples, the implant 1000 may be positioned entirely within the delivery lumen 1025. In the configuration illustrated in FIG. 10B, the bypass channel 245 fluidly couples the bore 215 to the fluid chamber 235 around the plunger seal 225. As the drive shaft 530 and the drive seal 230 apply pressure to the working fluid 1020 in the fluid chamber 235, the working fluid 1020 may move into the bore 215 through the bypass channel 245.

The plunger 210 may be retained in the position of FIG. 10B against further force applied to the drive seal 230. For example, in some embodiments, the second end 255 of the plunger 210 may be flared, and the plunger interface 240 may be configured to engage the second end 255 to limit advancement. Additionally, or alternatively, the implant bay 110 or the nozzle 105 may comprise a plunger stop 1030 configured to engage some portion or feature of the plunger 210, such as the second end 255 of the plunger 210, to prevent further advancement. In yet other examples, some embodiments of the delivery lumen 1025 may be tapered, which can prevent further advancement of the plunger 210 into the delivery lumen 1025. For example, the diameter of the delivery lumen 1025 may decrease as it gets further from the implant bay 110.

With the plunger 210 retained, additional pressure applied by the drive seal 230 on the working fluid 1020 can move the working fluid 1020 through the bypass channel 245 and the bore 215, as illustrated in the example of FIG. 10C. Movement of the working fluid 1020 from the bore 215 into the delivery lumen 1025 under pressure from the drive seal 230 can increase the pressure and flow rate of the working fluid 1020 in the delivery lumen 1025 behind the implant 1000, which can advance the implant 1000 further through the delivery lumen 1025 until the implant 1000 is ejected.

Figure 11A:
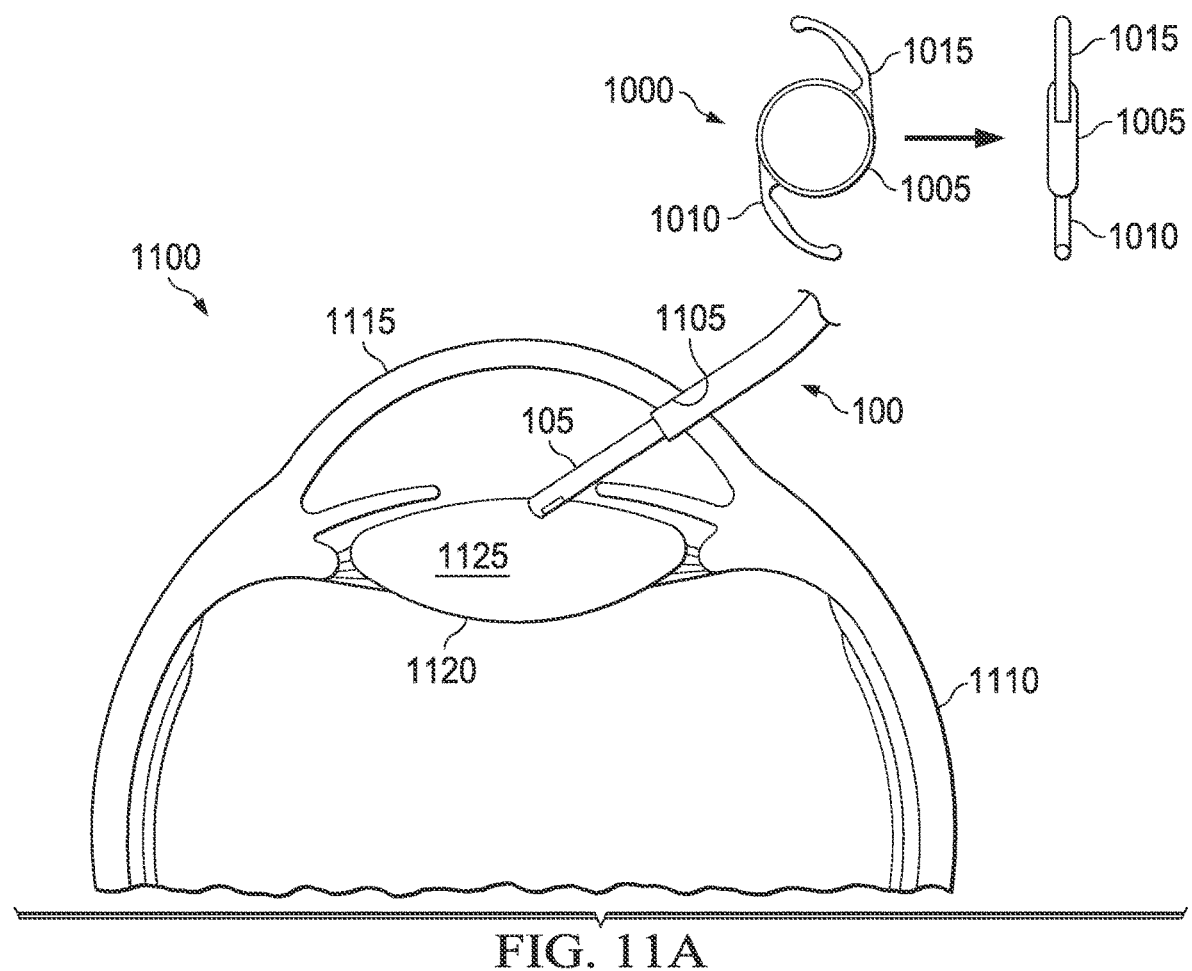
FIG. 11A-11B are schematic diagrams illustrating an example application of the system of FIG. 1 to insert an implant into an eye.
Figure 11B:
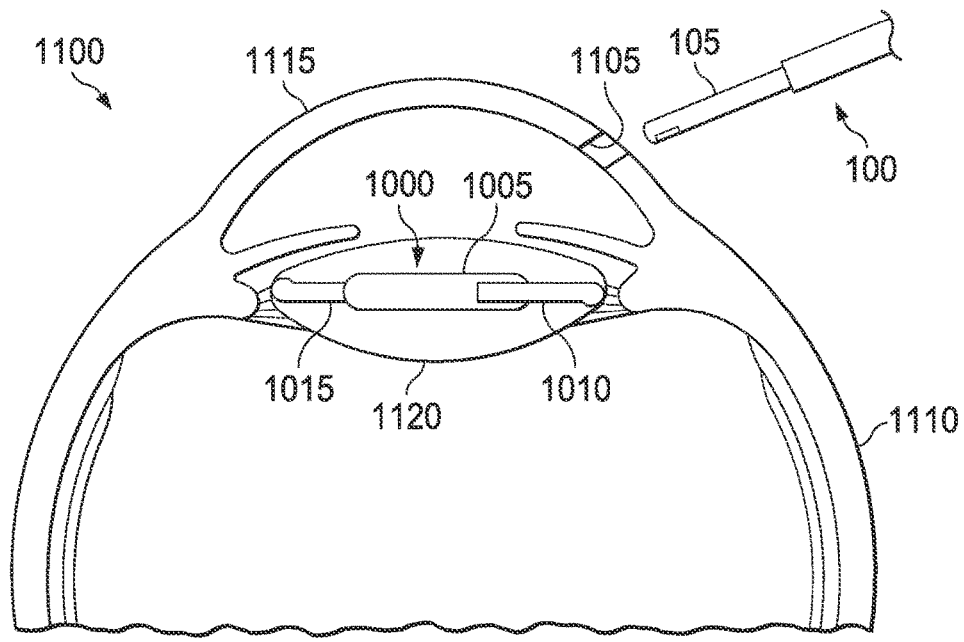

FIGS. 11A-11B are schematic diagrams further illustrating an example use of the system 100 to deliver the implant 1000 to an eye 1100. As illustrated, an incision 1105 may be made in the eye 1100 by a surgeon, for example. In some instances, the incision 1105 may be made through the sclera 1110 of the eye 1100. In other instances, an incision may be formed in the cornea 1115 of the eye 1100. The incision 1105 may be sized to permit insertion of a portion of the nozzle 105 in order to deliver the implant 1000 into the capsular bag 1120. For example, in some instances, the size of the incision 1105 may have a length less than about 3000 microns (3 millimeters). In other instances, the incision 1105 may have a length of from about 1000 microns to about 1500 microns, from about 1500 microns to about 2000 microns, from about 2000 microns to about 2500 microns, or from about 2500 microns to about 3000 microns.

After the incision 1105 is made, the nozzle 105 can be inserted through the incision 1105 into an interior portion 1125 of the eye 1100. The system 100 can then eject the implant 1000 through the nozzle 105 into the capsular bag 1120 of the eye 1100, substantially as described above with reference to FIGS. 10A-10C. In some applications, the implant 1000 may be delivered with one or more of the leading haptic 1010 and the trailing haptic 1015 in a folded configuration and can revert to an initial, unfolded state, within the capsular bag 1120, as shown in FIG. 11B. The capsular bag 1120 can retain the implant 1000 within the eye 1100 in a relationship relative to the eye 1100 so that the optic body 1005 refracts light directed to the retina (not shown). The leading haptic 1010 and the trailing haptic 1015 can engage the capsular bag 1120 to secure the implant 1000 therein. After dispensing the implant 1000 into the capsular bag 1120, the nozzle 105 may be removed from the eye 1100 through the incision 1105, and the eye 1100 can be allowed to heal over a period of time.

The systems, apparatuses, and methods described herein may provide significant advantages. For example, some embodiments may be particularly advantageous for delivering intraocular lenses, including fluid-filled accommodating lenses, which can present unique challenges for delivery. Some embodiments can compress a relatively large lens to fit through an acceptably small incision, manage deformation caused by shifting fluid during compression and exit from a nozzle, and execute delivery in a predictable and controlled manner. Additionally, some embodiments can reduce system complexity and the number of delivery steps while maintaining haptic position consistency. Some embodiments may also reduce the amount of working fluid for delivery.

Additionally, or alternatively, the magnetic coupling between the drive shaft 530 and the driver 620 can allow sealed components within the housing 505 to be removed, which may be advantageous for sterilization and other maintenance, as well as increasing reusability and reducing environmental impacts. For example, steam from autoclaving can present challenges to batteries and other electronics and enclosing these components within the housing 505 and the containment seal 840 can substantially reduce or eliminate some of these challenges by fluidly isolating them from steam during an autoclave cycle.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations, the nozzle 105, the implant bay 110, the actuator 115, the drive module 120 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

The invention claimed is:

1. An apparatus for operating an implant delivery device, the apparatus comprising:
a lead screw;
a lead nut threaded to the lead screw, the lead nut configured to rotate around the lead screw;
a follower coupled to the lead nut;
a driver magnetically coupled to the follower;
a containment seal between the driver and the follower; and
a motor coupled to the driver, the motor configured to operate the driver to rotate the follower and the lead nut to move the lead screw linearly.

2. The apparatus of claim 1, further comprising a lead sleeve that couples the follower to the lead nut.

3. The apparatus of claim 2, wherein the lead sleeve comprises an open cylinder configured to receive at least a portion of the lead screw.

4. The apparatus of claim 1, wherein:
the follower comprises a first magnetic rotor; and
the driver comprises a second magnetic rotor having an open cylinder disposed concentrically around the first magnetic rotor.

5. The apparatus of claim 1, wherein:
the follower comprises a first plurality of magnets; and
the driver comprises a second plurality of magnets.

6. The apparatus of claim 5, wherein:
the first plurality of magnets are arranged with alternating polarity; and
the second plurality of magnets are arranged with alternating polarity.

7. The apparatus of claim 1, wherein:
the follower comprises a first plurality of magnets disposed in a cylindrical array; and
the driver comprises a second plurality of magnets disposed in a cylindrical array around the first plurality of magnets.

8. The apparatus of claim 1, wherein the containment seal fluidly isolates the motor from the follower.

9. An apparatus for delivering an implant into an eye, the apparatus comprising:
a nozzle having a delivery lumen;
an implant bay coupled to the nozzle;
an actuator;
a follower;
a lead nut coupled to the follower;
a lead screw threaded to the lead nut and configured to be coupled to the actuator;
a driver magnetically coupled to the follower;
a containment seal between the driver and the follower; and
a motor coupled to the driver, the motor configured to operate the driver to move the follower so that the lead nut rotates around the lead screw, the lead screw moves linearly, and the actuator moves the implant through the delivery lumen.

10. The apparatus of claim 9, wherein:
the follower comprises a first magnetic rotor; and
the driver comprises a second magnetic rotor having an open cylinder disposed concentrically around the first magnetic rotor.

11. The apparatus of claim 9, wherein the containment seal fluidly isolates the driver from the follower.

12. The apparatus of claim 9, wherein:
the actuator comprises a housing and plunger operable to move linearly within the housing; and
the lead screw is coupled to the plunger.

13. The apparatus of claim 9, wherein:
the actuator comprises a housing, a plunger disposed within the housing and operable to move linearly from a first position to a second position to advance the implant from the implant bay to the delivery lumen, a bore fluidly coupled to the delivery lumen through the plunger, and a fluid chamber; and the lead screw is configured to move the plunger from the first position to the second position and move fluid from the fluid chamber to the delivery lumen through the bore in the second position.

14. An apparatus for delivering an implant to an eye, the apparatus comprising:

a nozzle comprising a delivery lumen;

an actuator comprising a plunger, a bore fluidly coupled to the delivery lumen through the plunger, and a fluid chamber;

a motor magnetically coupled to the actuator; and a containment seal that fluidly isolates the motor from the actuator;

wherein, the motor is configured to move the plunger linearly from a first position to a second position to advance the implant into the delivery lumen and to move fluid from the fluid chamber to the delivery lumen through the bore in the second position to eject the implant through the nozzle.

* * * * *